United States Patent [19]

Brumm et al.

[11] Patent Number: 4,830,963

[45] Date of Patent: May 16, 1989

[54] PRODUCTION OF ACETIC ACID BY AN IMPROVED FERMENTATION PROCESS

[75] Inventors: Phillip J. Brumm; Rathin Datta, both of Chicago, Ill.

[73] Assignee: Michigan Biotechnology Institute, Lansing, Mich.

[21] Appl. No.: 713,937

[22] Filed: Mar. 20, 1985

[51] Int. Cl.$^4$ .......................... C12P 7/54; C12R 1/145
[52] U.S. Cl. .................................... 435/140; 435/813; 435/842
[58] Field of Search .................... 435/140, 172.1, 253, 435/289, 290, 801, 813, 842, 139; 426/17

[56] References Cited

U.S. PATENT DOCUMENTS 4,282,323  8/1981  Yates .................................. 435/140

OTHER PUBLICATIONS

Wang et al., "Elucidation of Growth Inhibition and Acetic Acid Production by *Clostridium Thermoaceticum*"; *Appl. & Env. Micro.*, V. 47, N. 2, (Feb. 1984), pp. 294–298.

*Primary Examiner*—Elizabeth C. Weimar
*Attorney, Agent, or Firm*—Quarles & Brady

[57] ABSTRACT

A formate salt is used as part of the fermentable carbon-containing material in an anaerobic fermentation to produce acetic acid. Acetate salt formed in the fermentation is converted to free acetic acid with formic acid, which in turn is changed to formate salt. This formate salt then is used as a carbon source for another fermentation.

4 Claims, No Drawings

4,830,963

PRODUCTION OF ACETIC ACID BY AN IMPROVED FERMENTATION PROCESS

FIELD OF THE INVENTION

This invention relates to a fermentation method for producing acetic acid. The free acid is obtained by acidification with formic acid to give a fermentable by-product.

BACKGROUND OF THE INVENTION

The production of organic chemicals by microorganisms is well known to those familiar with the fermentation art. Such fermentation reactions frequently produce a variety of products in dilute aqueous solutions. The expense of separating the chemicals from each other and from the large volume of water has been so great that production of chemicals by fermentation has not been able to compete with production of the same chemicals from fossil fuel sources. However, the gradual depletion of petroleum fossil fuel with the resultant increase in prices of petrochemical feedstocks has revived interest in such fermentation reactions which can convert carbohydrates that are renewable raw materials into simple organic chemicals.

Among the chemicals which can be produced by anaerobic fermentation of carbohydrates is acetic acid. However, the microorganisms which produce this acid are most productive in growth media or near a neutral pH. When attempts are made to run these fermentations at low pH where the free acid is produced, the organisms do not grow well and only a very low concentration of the acid is obtained. For this reason, alkali is added during the fermentations to maintain the pH near neutrality. As a result, the fermentations produce acetate salts rather than free acetic acid.

It is very difficult to separate the acetate salts from the dilute aqueous fermentation media in which they are produced. Moreover, the free acid is the product of interest to the chemical industry. For this reason, mineral acids are generally added at the end of the fermentation in order to convert the acetate salts to free acetic acid. This acidification produces quantities of inorganic salts as by-products which are of little value. Their disposal also increases the cost of the process.

A fermentation process has now been developed wherein the acetate salt is converted to free acetic acid by means of formic acid. The free acetic acid is obtained together with a formate salt. This salt can then be used as the carbon source in the fermentation process. Thus, the present method produces free acetic acid in good yield and high concentration without giving the useless by-products formed in the prior processes.

It has now been discovered that the lactate fermentation proceeds more rapidly and without the need for pH control if a formate salt is used with the lactate as the carbon source in the first fermentation step of that process. Furthermore, the acidification step of that process, which produces lactic acid, can be completed by the addition of formic acid. This produces a mixture of lactate and formate salts which are used as the carbon source for the first fermentation step. Thus, the present process is a valuable supplement to the lactate fermentation process.

As noted above, the fermentation of carbohydrates to acetic acid is run near a neutral pH where the microorganisms are most productive. To maintain this pH, alkali is added to neutralize hydrogen ions formed in the fermentation. The fermentation of formate on the other hand produces hydroxyl ions. If formate is used as part of the carbon source along with carbohydrates, no addition of alkali is needed to maintain the desired pH. Hydroxyl ions produced by fermentation of formate neutralize hydrogen ions produced by fermentation of carbohydrates. Thus, the present process is also a valuable supplement to the carbohydrate fermentation process.

SUMMARY OF THE INVENTION

In accordance with the present invention, there is provided a process for the preparation of acetic acid. This process comprises the steps of:

(a) fermenting a fermentation medium containing a formate salt and other carbon-containing fermentable material with a microorganism under conditions suitable for converting said formate salt and fermentable material to a salt of acetic acid;

(b) acidifying the salt of acetic acid formed in Step (a) with formic acid to give a solution comprising acetic acid and a formate salt;

(c) separating the acetic acid from the formate salt; and (d) recycling the formate salt from Step (c) for use in Step (a).

DETAILED DESCRIPTION OF THE INVENTION

The process of this invention involves the fermentation of a formate salt with additional fermentable material to prepare acetic acid. Any microorganism capable of converting a formate salt to a salt of acetic acid can be used in the fermentation. However, it is preferable to use a microorganism that forms acetic acid as the sole product. *Clostridium thermoaceticum,* hereafter abbreviated *C. thermoaceticum,* is such an organism.

A preferred strain of *C. thermoaceticum* is the mutant strain disclosed in U.S. patent application Ser. No. 474,608, filed Mar. 11, 1983 now U.S. Pat. No. 4,513,084. This strain bears the American Type Culture Collection Deposit No. ATCC 39289. It is capable of fermenting formate in the presence of a fermentable carbohydrate and can be adapted to grow on a medium having a formate concentration as high as 0.5M.

The fermentable carbohydrate used a a carbon source in the fermentation can be any carbohydrate that is fermented to acetate by the microorganism used. Suitable carbohydrates include: dextrose, fructose, sucrose, starch hydrolyzates, and similar materials.

When the fermentation is complete, the mixture is acidified with formic acid to convert the acetate salt to free acetic acid. The formic acid is converted simultaneously to the formate salt. Dilute solutions of formic acid can be used for the acidification step. Such solutions of formic acid are readily produced by catalytic reduction of $CO_2$ or hydration of CO and are much less expensive than concentrated formic acid.

The acetic acid is separated from the fermentation mixture by well-known procedures. These include: solvent extraction, adsorption on a solid adsorbent, and distillation. Before the acid is separated from the fermentation mixture, it may be desirable to remove the cells and cell debris from the fermentation mixture. This can be done by conventional means, such as filtration and centrifugation.

After the acid has been removed from the mixture, the residue which contains the formate salt and other nutrients is reused to make up the fermentation medium for the first fermentation step. Thus, the process efficiently uses the formate salt produced in the acidification step as the raw material for the fermentation. The net reaction is the conversion of a carbohydrate and a dilute solution of formic acid to acetic acid. The only by-products of the process are the spent cells of the microorganisms which make a useful supplement to animal feed.

The following examples illustrate certain embodiments of the present invention. Unless otherwise stated, all proportions and percentages are provided on the basis of weight.

Acetate, formate, and dextrose concentrations were determined using high-performance liquid chromatography (HPLC). A sample of fermentation mixture was centrifuged at about 10,000 x g for 10 minutes to pellet the cells. Components of the supernatant were chromatographed by elution with 0.06N $H_2SO_4$ from a cation-exchange resin in the hydrogen form. The eluted components were detected by means of a differential refractometer, plotted on a recorder and quantitated using an electronic integrator. The are underneath the curve which represents concentration of each component was reported as a percentage of the total are. The general procedure is that given in "Analyses of Carbohydrate Mixtures by Liquid Chromatography", *Am. Soc. Brew. Chem. Proc.*, 1973, pp. 43–46. The separations were made on a 1-foot HPX87 column in the hydrogen form, available from Bio-Rad Laboratories, Richmond, Calif.

EXAMPLE 1

Conversion of Formate and Dextrose to Acetic Acid

The strain of *C. thermoaceticum* used in this example is available from the American Type Culture Collection, Rockville, Md., as ATCC No. 39289.

Medium preparation and cultivation of samples were carried out using standard anaerobic techniques as described by Hungate, R. E., "A Roll Tube Method for Cultvation of Strict Anaerobes", in *Methods in Microbiology*, edited by J. R. Norris and D. W. Ribbons, Vol. 3B, Academic Press, New York, 1969, pp. 117–132, and by Miller and Wolin, *Appl. Microbiol.*, 27, 985 (1974).

The medium used for growth of the organism had the following composition:

| GROWTH MEDIUM | |
|---|---|
| Component | Concentration (g/liter) |
| Yeast Extract | 5.0 |
| Tryptone | 5.0 |
| $(NH_4)_2SO_4$ | 1.0 |
| $MgSO_4.7H_2O$ | 0.25 |
| $K_2HPO_4$ | 7.0 |
| $KH_2PO_4$ | 5.5 |
| $Na_2MoO_4.2H_2O$ | 0.002 |
| $Na_2WO_4.2H_2O$ | 0.003 |
| $ZnCl_2$ | 0.00005 |
| $Na_2SeO_3$ | 0.0002 |
| $NiCl_2.6H_2O$ | 0.00002 |
| Resazurin Indicator | 0.002 |
| Ethylenediaminetetraacetic Acid Disodium Salt Dihydrate | 0.005 |
| $MnCl_2.4H_2O$ | 0.005 |
| $H_3BO_3$ | 0.0001 |
| $AlK(SO_4)_2.12H_2O$ | 0.0001 |
| $CuCl_2.2H_2O$ | 0.00001 |

A solution of the growth medium was brought to boiling under a $CO_2$ sparge. Then 0.5 g of sodium thioglycollate and 10 g of $NaHCO_3$ per liter of medium were added. When the medium was fully reduced as shown by the resazurin indicator, it was sparged with $CO_2$ while cooling. Then 30-ml Bellco anaerobic tubes (Bellco Glass Inc., Vineland, N.J.) were filled with 10 ml of the medium under an atmosphere of $N_2:H_2:CO_2$ (90:5:5) in an anaerobic glove box, stoppered, crimped, and sterilized. Dextrose was prepared as a 50% w/v solution by boilin under $CO_2$ sparge for 30 minutes. It was then cooled under $CO_2$ and sterilized. Sufficient dextrose solution was added to the medium to give a concentration of 15 g/l.

A culture of *C. thermoaceticum* was grown in Bellco tubes containing the medium for 72 hours at 60° c. A 1.0-ml aliquot of this culture was transferred to 10 ml of the standard medium which contained 0.1M sodium formate in addition to the dextrose as a carbon source. The cells were serially transferred every 72 hours into media containing increasing concentrations of formate in addition to the dextrose. After four transfers, they grew in a medium containing 0.5M formate.

Fermentations of mixtures of dextrose and formate were carried out in 160-ml serum vials containing about 100 ml of medium. The inoculum was 10 ml of a 24-hr culture of *C. thermoaceticum* that had been adapted to grow in the presence of 0.5M formate. The medium was the same as that used for growth of the organism except that twice the concentrations of glucose, yeast extract, and tryptone were used. The medium also contained 0.4M or 0.5M formate (prepared from formic acid which had been neutralized with sodium hydroxide).

The fermentations wer run for 96 hrs at 60° C. Then the liquid was separated from cells of the microorganism and analyzed by HPLC. The results given in Table I show that both formate and dextrose are converted to acetate in this fermentation.

TABLE I

| Run No. | pH Start | pH After 96 hrs | Dextrose (g/l) Start | Dextrose (g/l) 96 hrs | Formate (g/l) Start | Formate (g/l) 96 hrs | Acetate (g/l) Start | Acetate (g/l) 96 hrs |
|---|---|---|---|---|---|---|---|---|
| 1 | 7.0 | 6.6 | 30 | 13.2 | 18.4 | 0.4 | 0 | 16.3 |
| 2 | 7.3 | 6.7 | 30 | 13.6 | 23 | 0.3 | 0 | 17.1 |

When 100 ml of the solution of Run No. 2 was acidified with 12 ml of a dilute solution of formic acid containing 1.2 g of the acid, the resulting pH was 4.19. The concentration of free acetic acid was 13.3 g/l.

EXAMPLE 2

Fermentation of Formate and Dextrose-Time Study

The fermentation was carried out following the general procedure of Example 1. Samples were withdrawn at intervals and analyzed by HPLC. Bacterial growth was determined by measuring the optical density of the mixture at 540 nm using a Spectronics 20 spectrophotometer. The results given in Table II show that acetate is formed by the simultaneous conversion of formate and dextrose.

TABLE II

| Time (hrs) | pH | Optical Density 540 nm | Dextrose (g/l) | Formate (g/l) | Acetate (g/l) |
|---|---|---|---|---|---|
| 0 | 7.2 | 0.07 | 23.6 | 12.5 | 1.1 |
| 24 | 7.2 | 0.10 | 23.2 | 11.9 | 1.2 |
| 42 | 7.2 | 0.54 | 22.4 | 10.2 | 2.2 |
| 48 | 7.2 | 0.60 | 21.9 | 8.9 | 3.0 |

TABLE II-continued

| Time (hrs) | pH | Optical Density 540 nm | Dextrose (g/l) | Formate (g/l) | Acetate (g/l) |
|---|---|---|---|---|---|
| 70 | 7.3 | 1.0 | 19.6 | 3.8 | 6.5 |
| 162 | 7.0 | 1.3 | 13.4 | 0.5 | 12.1 |

EXAMPLE 3

Fermentation of Formate and Lactate

The fermentation was conducted in serum vials following the general procedure of Example 1. In this case, the dextrose was replaced by lactate (prepared from DL--lactic acid which had been neutralized with sodium hydroxide). After a lag of about 60 hrs, the fermentation proceeded with simultaneous conversion of lactate and formate to acetate. The results given in Table III also show that the Ph is maintained in the medium without the need to add alkali to maintain pH control as is required when the medium contains lactate as the sole carbon source.

TABLE III

| Time (hrs) | pH | Optical Density 540 nm | Lactate (g/l) | Formate (g/l) | Acetate (g/l) |
|---|---|---|---|---|---|
| 0 | 6.4 | 0.04 | 28.7 | 11.7 | 2.2 |
| 61 | 6.5 | 0.09 | 27.8 | 10.4 | 2.5 |
| 132 | 6.88 | 1.0 | 16.9 | 0.1 | 17.6 |
| 160 | 6.7 | 1.0 | 11.4 | 0.1 | 22.9 |

Thus, it is apparent that there has been provided, in accordance with the invention, a process for the preparation of acetic acid that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the rapid, microbial preparation of acetic acid without the need for pH control which comprises the steps of:
   (a) fermenting a fermentation medium containing a carbon-containing fermentable material and a formate salt with a microorganism having the identifying properties of *Clostridium thermoaceticum* ATCC No. 39289 under conditions suitable for converting said formate salt and carbon-containing fermentable material to a salt of acetic acid;
   (b) acidifying the salt of acetic acid formed in Step (a) with formic acid to give a solution comprising acetic acid and a formate salt;
   (c) separating the acetic acid from the formate salt; and
   (d) recycling the formate salt from Step (c) for use in Step (a).

2. The process of claim 1 wherein the carbon-containing fermentable material is a lactate salt.

3. The process of claim 1 wherein the carbon-containing fermentable material is a fermentable carbohydrate.

4. The process of claim 3 wherein the fermentable carbohydrate is dextrose.

* * * * *